United States Patent [19]
Palmer

[11] 4,186,206
[45] Jan. 29, 1980

[54] TREATMENT OF SWINE DYSENTERY

[75] Inventor: Geoffrey H. Palmer, Crawley, England

[73] Assignee: Beecham Group Limited, England

[21] Appl. No.: 926,644

[22] Filed: Jul. 21, 1978

[30] Foreign Application Priority Data

Jul. 27, 1977 [GB] United Kingdom ............... 31475/77

[51] Int. Cl.$^2$ ........................................... A61K 31/35
[52] U.S. Cl. .................................................. 424/283
[58] Field of Search ....................................... 424/283

[56] References Cited

PUBLICATIONS

Fuller et al.,-Chem. Abst., vol. 76, (1972), p. 97902a.
Barrow et al.,-Chem. Abst., vol. 78, (1973), p. 96086s.

*Primary Examiner*—Sam Rosen
*Attorney, Agent, or Firm*—Jacobs & Jacobs

[57] ABSTRACT

Swine dysentery may be treated or prevented by administering to a swine an effective amount of pseudomonic acid, a nontoxic salt thereof or nontoxic ester thereof.

9 Claims, No Drawings

TREATMENT OF SWINE DYSENTERY

This invention relates to a method for the treatment of swine dysentery.

British Pat. No. 1,395,907 discloses that pseudomonic acid, of formula (I):

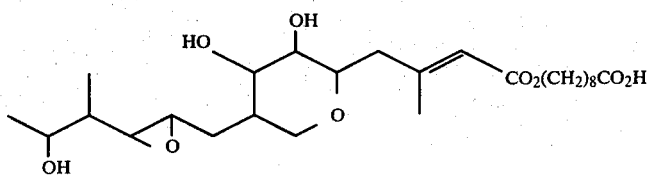

(I)

and salts and esters thereof, have anti-bacterial activity.

Swine dysentery is a mucohemorrhagic diarrhoeal disease that primarily affects weaning pigs but can affect larger pigs.

We have now discovered that pseudomonic acid, its salts and its esters, give effective treatment of this severe disease.

Accordingly the present invention provides a method of treatment of swine dysentery, which method comprises administering to a swine an effective amount of pseudomonic acid or a non-toxic salt or ester thereof.

It is believed that pseudomonic acid has the absolute stereochemistry as shown in formula (IA):

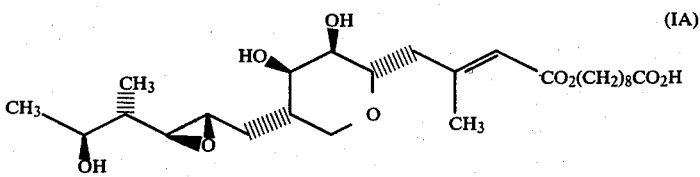

(IA)

Suitable non-toxic salts of pseudomonic acid which may be administered include metal salts, e.g. aluminium, alkali metal salts such as sodium or potassium, alkaline earth metal salts such as calcium or magnesium, and ammonium or substituted ammonium salts for example those with lower alkylamino such as triethylamine, hydroxy-lower alkylamines such as 2-hydroxyethylamine, bis-(2-hydroxyethyl)-amino or tri-(2-hydroxyethyl)-amine, cycloalkylamines such as bicyclohexylamine, or with procaine, dibenzylamine, N,N-dibenzylethylene-diamine, 1-ephenamine, N-ethylpiperidine, N-benzyl-$\beta$-phenethyl-amine, dehydroabietylamine, N,N'-bis-dehydroabietylethylenediamine, or bases of the pyridine type such as pyridine, collidine or quinoline.

Preferred salts are alkali metal salts.

Suitable esters include alkyl, aryl and aralkyl groups, any of which may be substituted with a hydroxy, amino or halogen groups. For example the ester group may be a $C_{1-6}$ alkyl group in particular, methyl, ethyl, n- or iso-propyl, n, sec-, iso or tert-butyl; a halo-($C_{1-6}$)-alkyl group such as trifluoromethyl, 2,2,2-trichloroethyl; an aminoalkyl group such as aminomethyl, 2-aminoethyl; hydroxymethyl, hydroxyethyl; phenyl; substituted phenyl; or a benzyl group.

Preferred esters are $C_{1-6}$ alkyl esters.

For administration the pseudomonic acid, salt or ester thereof, will be formulated into a suitable composition.

For oral administration for example the active agent may be formulated into tablets, capsules, granules, powders and the like; or as a liquid preparation; or may simply be added to the swine's feed and/or drinking water.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For parenteral administration, fluid unit dosage forms may be prepared utilizing the active agent and a sterile vehicle, water being preferred. The active agent, depending on the vehicle and concentration used, can be either suspended or dissolved in the vehicle. In preparing solutions the active agent can be dissolved in water for injection and filter sterilized before filling into a suitable vial or ampoule and sealing. Advantageously, adjuvants such as a local anesthetic, preservative and buffering agents can be dissolved in the vehicle. To enhance the stability the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the active agent is suspended in the vehicle instead of being dissolved and sterilization cannot be accomplished by filtration. The active agent can be sterilized by exposure to ethylene oxide before suspending in the sterile vehicle. Advantageously, a surfactant or wetting agent is included in the composition to facilitate uniform distribution of the active agent.

When the pseudomonic acid or salt or ester is administered parenterally, the solution to be injected may contain from about 10 to 500 mg/ml, preferably about 100 mg/ml of the active ingredient. Preferably the solution or suspension is injected intramuscularly or subcutaneously.

A suitable dose for both parenteral and oral administration is from 0.5 to 250 mg/kg per day, preferably from 5 to 20 mg/kg per day.

A particularly preferred method of administration of the active agent is to add it to the swine's drinking water. We have found that a concentration of active ingredient in the drinking water of about 30 to 600 $\mu$g/ml, preferably 50 to 150 $\mu$g/ml, for example 75 to 100 $\mu$g/ml, is suitable. In such a case, it is often advantageous to prepare an aqueous solution of the active compound and add the solution to the swine's drinking water.

The active compound may also be administered to swine by addition to the swine's feed either by admixture with a commercial dry feed, or addition in a premix or feed supplement. For such an administration, the active compound will generally be present at a level of 100 to 1000 $\mu$g/gm of feed, preferably from 100 to 300 $\mu$g/gm.

A premix or feed supplement may contain from about 0.5% by weight to 99% by weight, preferably from 1 to 10% by weight, of pseudomonic acid or salt or ester thereof, dispersed in an inert carrier or diluent such as, for example, processed grain by-products such as soyabean mill runs and ground rice hulls, inorganic carriers such as limestone flour, soya flour or oyster shell flour, anticaking agents such as calcium silicate and the like.

The active compounds may also be administered prophylactically to swine susceptible to swine dysentery. In such a case, lower dosage than for therapeutic treatment is usually sufficient for prophylactic use. For example the level to be administered in feed will generally be from 10 $\mu$g/gm of feed, upwards.

Biological Data

1. Objective

This study was carried out to provide data on the chemotherapeutic efficacy of Pseudomonic acid against experimentally induced swine dysentery.

2. Methods 2.1. Animals 12 pigs were housed in second stage early weaner cages and fed a control diet (no antibiotics or growth promoters) for four days prior to and throughout the experiment.

2.2. Pre infection studies

Prior to infection pigs were:
  (a) Weighed
  (b) Blood sampled for PCV and inhibitors.
  (c) Rectal swabs were taken and examined for Salmonellae by culture and T.Hyodysenteriae by phase microscopy. No Salmonella or Treponema were detected.

2.3. Infection

Each pig was given 30 mls of a homogenate of colonic material from pigs severely affected with swine dysentery by mouth via a catheter tipped syringe.

2.4 Chemotherapy

Pigs were observed daily and considered to be dysenteric by the following criteria: either
  (a) Check in bodyweight and
  (b) Faecal score of 2 to 3 or
  (c) Faecal score of 3 (blood/mucus in faeces) and allocated randomly to the following treatments:
    (i) Control—no medication
    (ii) Pseudomonic acid at 77.2 mcg/ml in the drinking water.

The treatments were allowed "adlibitum" and supplied via nipple drinkers.

Treatments were continued for 5 days when each pig was slaughtered and a post mortem carried out.

2.5 Records

The following observatiions were made for each pig:
1. Bodyweights: every two days until evidence of dysentery then daily.
2. Faecal score Faecal consistency was scored daily as follows:
0—normal
1—loose
2—liquid
3—liquid with mucus and blood
3. Post mortem At post mortem the pigs were examined for dysentery symptoms and scored as follows:
  (a) Faecal consistency as in 2.
  (b) Mucosal surface of colon:
    0—normal
    1—slight patchy inflammation
    2—part of colon with lesions
    3—severe—mucohaemorrhagic colitis of whole colon
  (c) Serosal surface of colon.
    0—normal
    1—evidence of inflammation (patchy)
    2—moderate inflammation
    3—severe inflammation and swollen colonic glands
3. Results All the pigs challenged developed symptoms of swine dysentery within 5–21 days, and most had bloody faeces at some time during the experiment.

One pig died on the 4th day after being allocated to the control group.

Bodyweights

Table 1 and 2 show the bodyweights and liveweight change in kgs and individual animals allocated to the two treatments.

Significant differences were observed in weight gains over the 5 days experimental periods, the Pseudomonic acid medicated group showing increased weight gains compared to the control group, where a net loss of 2.08 kg (11% of bodyweight) was observed.

Faecal scores

Table 3 and 4 show the faecal scores. All animals on the control group were dysenteric over the experimental period (faecal score 2–3). In contrast all animals in the medicated group had normal (0) or only slight looseness (1) within 2 to 4 days of commencing treatment.

Post Mortems (Table 5)

At post mortem all control pigs had blood in their colon contents and severe mucohaemorrhagic colitis (score 3) over the entire mucosal surface of the colon.

The inflammation was evident on the serosal surface of the colon.

In contrast in the medicated group there was a complete absence of any evidence of dysentery lesions or inflammation. These pigs were considered to be clinically normal.

Side Effects

No symptoms were observed which could be attributed to the Pseudomonic acid. All pigs appeared to drink "normally", i.e. no evidence of unpalatability.

Summary

Pseudomonic acid (at 77.2 mcg/ml) when given in the drinking water was effective in the treatment of experimentally induced swine dysentery, on the scores of increased bodyweight and absence of lesions at post mortem (5 days of treatment). A beneficial response to treatment was observed 2-4 days after medication commenced when dysentery symptoms had largely disappeared (near normal faeces). In contrast control animals remained dysenteric over the experimental period and there was 1 death.

The following Examples illustrate a number of compositions which may be employed in the method of this invention:

EXAMPLE 1

Premix

A premix is made up from the following ingredients:
Pseudomonic acid 100 g
Limestone flour 900 g

EXAMPLE 2

Aqueous Suspension for Injection

A solution of lecithin (1 part), polyvinylpyrrolidone (5 parts) and methyl propyl p-hydroxybenzoate (1 part) was added to a mixture of pseudomonic acid (250 parts), trisodium citrate dihydrate (10 parts) and sodium chloride (2 parts).

The resulting granules were dried and milled and the powder sealed in multidose vials.

For use, sterile water was injected into vials to give a suspension containing 100 mg/ml of active material.

EXAMPLE 3

Oily Suspension for Injection

A suspension for pseudomonic acid in ethyl oleate (10% w/v) was sealed in multidose vials.

TABLE 1

| | Bodyweights in kgs at:- | | | | | Control Unmedicated | |
|---|---|---|---|---|---|---|---|
| | | ←Treatment Period→ | | | | | |
| Pig No. | On Arrival | Day 1 | Day 2 | Day 3 | Day 4 | Day 5 | Liveweight Change | % L.W. Change |
| 1 | 17.00 | 17.25 | 16.00 | 14.00 | Died | | −3.25 | −18.84 |
| 2 | 17.50 | 16.50 | 16.50 | 17.00 | 16.50 | 16.25 | −0.25 | −1.52 |
| 3 | 19.00 | 17.50 | 16.25 | 16.50 | 16.00 | 16.00 | −1.50 | −8.57 |
| 4 | 16.50 | 17.25 | 17.00 | 16.00 | 15.50 | 15.00 | −2.25 | −13.04 |
| 5 | 20.00 | 20.00 | 18.50 | 18.00 | 17.50 | 17.50 | −2.50 | −12.50 |
| 6 | 20.50 | 22.25 | 22.00 | 21.25 | 20.00 | 19.50 | −2.75 | −12.36 |

TABLE 2

| | Bodyweights in kgs at:- | | | | | Pseudomonic Acid 77.2 ppm in water | |
|---|---|---|---|---|---|---|---|
| | | ←Treatment Period→ | | | | | |
| Pig No. | On Arrival | Day 1 | Day 2 | Day 3 | Day 4 | Day 5 | Liveweight Change | % L.W. Change |
| 1 | 17.50 | 16.00 | 16.25 | 16.25 | 17.00 | 17.50 | +1.50 | +9.38 |
| 2 | 18.00 | 17.25 | 16.25 | 17.25 | 18.50 | 18.50 | +1.25 | +7.25 |
| 3 | 18.75 | 18.00 | 19.00 | 19.50 | 20.50 | — | +2.50 | +13.89 |
| 4 | 19.00 | 19.25 | 18.00 | 19.25 | 20.00 | 21.00 | +1.75 | +9.09 |
| 5 | 17.00 | 19.00 | 19.50 | 20.50 | 20.75 | 21.25 | +2.25 | +11.84 |
| 6 | 18.50 | 18.25 | 19.00 | 20.50 | 22.25 | 22.75 | +4.5 | +24.66 |

TABLE 3

| | Control Unmedicated | | | | | |
|---|---|---|---|---|---|---|
| | Faecal Score | | | | | |
| Pig No. | On Arrival | Day 1 | Day 2 | Day 3 | Day 4 | Day 5 |
| 1 | 0 | 2 | 3 | 3 | died | |
| 2 | 0 | 2 | 3 | 3 | 2 | 3 |
| 3 | 0 | 2 | 2 | 2 | 2 | 2 |
| 4 | 0 | 2 | 3 | 3 | 3 | 3 |
| 5 | 0 | 2 | 3 | 2 | 2 | 2 |
| 6 | 0 | 2 | 3 | 3 | 3 | 2 |

TABLE 4

| | Pseudomonic Acid Group | | | | | |
|---|---|---|---|---|---|---|
| | Faecal Score | | | | | |
| Pig No. | On Arrival | Day 1 | Day 2 | Day 3 | Day 4 | Day 5 |
| 1 | 0 | 3 | 3 | 2 | 1 | 1 |
| 2 | 0 | 1 | 2 | 1 | 1 | 1 |
| 3 | 0 | 2 | 2 | 1 | 0 | — |
| 4 | 0 | 3 | 3 | 2 | 1 | 0 |
| 5 | 0 | 3 | 3 | 1 | 0 | 0 |
| 6 | 0 | 3 | 2 | 0 | 0 | 0 |

TABLE 5

| | | Post Mortem Scores | | |
|---|---|---|---|---|
| Treatment | Pig No. | Colon Contents Score | Mucosal Surface Score | Serosal Surface Score |
| Control | 1 | 3 (Died) | 3 | 3 |
| | 2 | 3 | 3 | 2 |
| | 3 | 2 | 2 | 2 |
| | 4 | 2 | 3 | 3 |
| | 5 | 3 | 3 | 3 |
| | 6 | 3 | 3 | 2 |
| Pseudomonic Acid | 1 | 1 | 0 | 0 |
| | 2 | 0 | 0 | 0 |
| | 3 | 0 | 0 | 0 |
| | 4 | 0 | 0 | 0 |
| | 5 | 0 | 0 | 0 |
| | 6 | 0 | 0 | 0 |

I claim:

1. A method for the treatment of swine dysentery which comprises administering to an infected swine, an effective amount of pseudomonic acid, a non-toxic salt or non-toxic ester thereof.

2. A method according to claim 1 wherein the active compound is pseudomonic acid or an alkali metal salt thereof.

3. A method according to claim 2 wherein the active compound is sodium pseudomonate.

4. A method according to claim 1 wherein the active compound is administered in an amount of from 0.5 to 250 mg/kg of animal body weight per day.

5. A method according to claim 4 wherein the active compound is administered in an amount of from 5 to 20 mg/kg of animal body weight per day.

6. A method claim 1 wherein the administration is oral.

7. A method according to claim 6 wherein the active compound is added to the swine's drinking water.

8. A method according to claim 6 wherein the active compound is administered by addition to the swine's feed.

9. The method of treating swine dysentery which comprices administering pseudomonic acid, either as the free acid or as a non-toxic alkali metal or amine salt, in combination with the swine's drinking water at a concentration of about 30 to 600 µg/ml or with the swine's feed at a concentration of about 100 to 1000 µg/gm.

* * * * *